United States Patent [19]

Kebbekus

[11] 4,221,569

[45] Sep. 9, 1980

[54] CHROMATOGRAPHIC ANALYSIS OF GASEOUS SAMPLES CONTAINING REACTIVE SULFUR

[75] Inventor: Earle R. Kebbekus, Maplewood, N.J.

[73] Assignee: Will Ross, Inc., Dallas, Tex.

[21] Appl. No.: 16,715

[22] Filed: Mar. 1, 1979

[51] Int. Cl.$^2$ ............................................. G01N 31/08
[52] U.S. Cl. ................................. 23/232 C; 23/232 R; 252/372; 55/67; 55/73
[58] Field of Search .......................... 23/232 C, 232 R; 252/408, 372; 55/67, 73

[56] References Cited

U.S. PATENT DOCUMENTS

| | | | |
|---|---|---|---|
| 2,494,587 | 1/1950 | Shabaker | 252/372 X |
| 3,838,969 | 10/1974 | Dugan | 23/232 C |
| 4,127,386 | 11/1978 | Stahl | 23/232 R |

OTHER PUBLICATIONS

Chemical Abstracts, 83:151478b (1975).
A. G. Vitenberg et al., Anal. Chem., 49(1), 128–133 (Jan. 1977).
J. C. Hilborn et al., The Science of the Total Environment, 4, 97–106, Elsevier Scientific Publishing Co., Amsterdam, 1975.

*Primary Examiner*—Sidney Marantz
*Attorney, Agent, or Firm*—John A. Dhuey; Albert Tockman

[57] ABSTRACT

A carrier gas for chromatographic analysis of gaseous samples containing sulfur bearing molecules utilizes a sulfur-containing nucleophile mixed with the inert component of the carrier gas to deactivate sulfur reactive and adsorbtive sites in the analysis system and facilitates accurate analysis of the sample composition.

4 Claims, No Drawings

CHROMATOGRAPHIC ANALYSIS OF GASEOUS SAMPLES CONTAINING REACTIVE SULFUR

BACKGROUND OF THE INVENTION

Because of the generally corrosive nature of sulfur containing compounds and their often harmful effects in industrial processes and on the environment, it has become desirable to monitor and analyze for sulfur compounds to determine the content and type of material present. Preferred methods of analysis are those which are rapid, sensitive and specific. Classical analytic methods for determining total sulfur content are generally unsatisfactory particularly since it often is desirable to analyze for specific individual components in a mixture of sulfur compounds.

Gas chromatography has become a useful tool for the analysis of sulfur-containing pollutants. However, conventional chromatographic systems have not been entirely satisfactory to analyze for trace amounts of reactive sulfur compounds since the compounds have a tendency toward adsorption on or reaction with the column walls, packing and components. Prior attempts at solving those problems generally have been directed to total system design to eliminate adsorption or reaction. Typically, total system design is very expensive and such systems are impractical for many of the sites at which monitoring and analysis is necessary. Even glass, stainless steel and TEFLON ® polymer systems have not eliminated the problems of adsorption and reaction entirely and the analysis of trace amounts of sulfur compounds has remained a vexing problem.

SUMMARY OF THE INVENTION

The invention provides a gaseous composition which is used as a carrier gas in conventional gas chromatographic systems of varying design. In particular, the invention provides for a supply of sulfur-containing nucleophiles in an otherwise inert carrier gas to deactivate sites in the chromatographic system which are prone to the reaction with or adsorption of sulfur-containing compounds. The signal generated in the detector system by the presence of the sulfur-containing nucleophiles can be conveniently electronically bucked so that the resultant signal displayed is that generated by the sulfur containing compounds in the sample to be analyzed. Since the reactive and adsorptive sites are deactivated by the mixed carrier gas, substantially all of the sulfur containing compounds in the sample reach the detector and their concentration and presence can be ascertained with much greater accuracy than in systems employing a conventional carrier gas.

DESCRIPTION OF THE PREFERRED EMBODIMENTS

The invention is concerned particularly with a gaseous composition useful as a carrier gas in chromatographic systems, the gaseous composition consisting of a mixture of an analytically pure inert gas and a compound containing a nucleophilic sulfur atom, and methods of its use. Preferred sources of nucleophilic sulfur atoms are hydrogen sulfide, sulfur dioxide, lower alkyl mercaptans, aryl mercaptans, lower alkyl sulfides, aryl sulfides, lower alkyl disulfides, aryl disulfides and carbonyl sulfide.

For purposes of this invention, lower alkyl comprehends those straight and branched chain alkyl radicals having 1-7 carbon atoms inclusive, exemplified by methyl, ethyl, propyl, butyl, pentyl, hexyl, heptyl and the branched chain isomers thereof. Aryl comprehends phenyl, benzyl, tolyl, xylyl and napthyl.

Expecially preferred lower alkyl groups are those having 1 to 4 carbon atoms inclusive. Among aryl, phenyl, benzyl and tolyl are especially preferred.

The most reactive nucleophilic sulfur compounds such as hydrogen sulfide and sulfur dioxide are especially preferred since they rapidly deactivate reaction and adsorption sites in the system and to a large extent prevent slower, competing reactions from occurring. Among the lower alkyl mercaptans, methyl mercaptan and ethyl mercaptan are most preferred, and carbon disulfide is most preferred among the disulfide compounds.

In certain circumstances, it may be advantageous to combine the inert gas with two or more different compounds containing nucleophilic sulfur atoms.

For purposes of this invention, the term "inert gases" comprehends gases which are unreactive with respect to the chromatographic system. The inert gases which are preferred in the carrier gas are exemplified by nitrogen, argon, helium, neon, krypton, xenon and hydrogen, and it is preferred that analytically pure inert gases are employed to avoid contamination in the chromatographic systems by extraneous materials. Nitrogen, argon, hydrogen and helium are especially preferred. Lower molecular weight hydrocarbon gases such as methane, ethane, propane and the like may also be used.

The amount of compound having a nucleophilic sulfur atom required for effective deactivation of the reactive and adsorptive sites in the system will depend to some extent on the nature of the materials making up the system and the design of the detector system. A minimum effective amount is that which will substantially deactivate all of the sites in the system. That amount can be determined by running carrier gas mixtures of differing concentrations until a constant output signal is achieved. The maximum effective amount which can be used is that amount for which the output signal generated by the presence of the sulfur containing nucleophiles can be electronically bucked by the detector system. The bucking of that signal permits recording of the signal generated by only the sulfur containing compounds in the sample which is being analyzed. In that manner, an accurate analysis of the sample composition can be made.

In most systems currently being used for sulfur analysis, a concentration of deactivation compound in the carrier gas of more than 0.01 parts per million and less than 5.0 parts per million on a volume basis is considered satisfactory. An especially preferred range of concentration for the deactivation compound is less than 2.0 parts per million and more than 0.05 parts per million on a volume basis.

The carrier gas consisting of a mixture of an analyticaly pure inert gas and a compound containing a nucleophilic sulfur atom is useful for the analysis of samples containing sulfur compunds which can be analyzed by gas chromatographic techniques. For example, automobile exhaust, industrial stack gases and atmospheric air samples all are amenable to chromatographic analysis. The gaseous composition of this invention is particularly useful as a carrier gas for chromatographic systems to analyze for sulfur-containing compounds such as carbonyl sulfide, methyl mercaptan, ethyl mercaptan, sulfur dioxide, dimethyl sulfide and carbon dissulfide which may be present in those environments.

Examples

A Tractor Model 560 Gas Chromatograph equipped with a standard single channel Tractor Flame Photometric Detector was employed. Detector gas flows were 100 cm³/min. of hydrogen and 150 cm³/min. of air as measured on calibrated rotameters. The gas sampling port was a six port, 303 stainless steel valve installed in the column oven. Sampling loops were constructed of TEFLON ® polymer or 316 stainless steel. The sample mixtures were transported to the sampling port from a high pressure cylinder through a regulator and TEFLON ® polymer tubing. The detector output signal was fed to a Columbia Scientific Industries Supergrator integrator and a strip chart recorder. Carrier gas containing the deactivating compound was prepared in a high pressure cylinder and transported to the chromatograph through a regulator and 316 stainless steel tubing. For a number of column packing materials described in the literature as being suitable for analysis of gases containing sulfur compunds, a series of parallel comparisons using analytically pure carrier gas and a mixture of analytically pure carrier gas and a compound containing a nucleophilic sulfur atom were made.

The following procedure was employed. Carrier gas, either mixed or pure, was set at a given flow rate. The flame photometric detectors' flame was ignited and the detector was allowed to operate for a minimum of about 2 hours. After that equilibration period, a series of sequential sample injections were made of a gas mixture containing low concentrations of a representative sulfur compound, sulfur dioxide. All of the injections were made according to a rigid time schedule, i.e. the purge time for the sample loop was 1 minute and the vent time to atmospheric pressure was 10 seconds. The integration time was fixed dependent upon the elution time of the sample for the combination of column, flow rate and column temperature employed.

After results were obtained for a particular carrier gas, the carrier gas was switched. During the switching, the operating conditions of the detector were not changed, i.e. the flame continued to burn with no change in air and hydrogen flows to the detector. After the change in carrier gas was made, an equilibration period of three hours or more was observed. During that period, the column temperature was maintained constant, and care was taken to have maintained the same flow rate through the column for both carriers. Following the equilibration periods, a series of injections of the same sample were made following the same time schedule as observed for the previous carrier. Accordingly, chart areas in microvolts. seconds were generated for both carriers and a given sample under reproducible operating conditions.

The results are summarized in the following tables. In all cases the response for a given sample is enhanced when the mixed carrier is employed, demonstrating the deactivation accomplished by the mixed carrier gas consisting of the analytically pure inert gas and the compound containing a nucleophilic sulfur atom. As is apparent from the table results, the effect is most pronounced with the low concentration sample.

EXAMPLE 1

Column Employed: Chromosorb 105 (Polyaromatic porous bead polymer from Johns-Manville Corp.) in 2.5 foot Teflon ® (FEP) ⅛" OD tube Operated at 70° C. with carrier flow rate of 40 cm³/min.

Sample employed 10.3 ppm Sulfur dioxide in Nitrogen Balance gas. Sample volume ~2 ml. Sequential injection of mixture onto column, according to a rigid time schedule, when using Nitrogen and the Mixed Carrier Gas gave the following peak areas for sulfur dioxide.

| INJECTION | Peak Area, μV. sec | |
|---|---|---|
| | Nitrogen Carrier | Mixed Carrier |
| 1 | 5,838 | 8,574 |
| 2 | 17,772 | 20,737 |
| 3 | 24,112 | 28,952 |
| 4 | 28,413 | 39,631 |
| 5 | 31,084 | 40,048 |
| 6 | 33,163 | 43,729 |
| 7 | 34,554 | 46,621 |
| 8 | 36,223 | 48,742 |
| 9 | 34,257 | — |

EXAMPLE 2(a)

Column Employed: Porapak QS (Porous bead copolymer of ethylvinylbenzene and divinylbenzene-silanized) Waters Associates in 1.5 foot Teflon ® (FEP) ⅛" OD tube Operated at 40° C.

Sample employed 10.3 ppm Sulfur dioxide in Nitrogen balance gas. Sample volume ~2 cm³. Sequential injections of mixture onto the column, according to a rigid time schedule, when using nitrogen and the mixed carrier gas gave the following peak areas for sulfur dioxide

| INJECTION | Peak Area, μV. sec | |
|---|---|---|
| | Nitrogen Carrier | Mixed Carrier |
| 1 | 85518 | 160,360 |
| 2 | 109354 | 175,412 |
| 3 | 117628 | 182,060 |
| 4 | 123168 | 183,224 |
| 5 | 126492 | 186,308 |
| 6 | 129034 | 185,256 |

EXAMPLE 2(b)

Sample employed: 0.5 ppm Sulfur dioxide in Nitrogen balance gas. (Other Parameters the same as Example 3 (a)

| INJECTION | Peak Area, μV. sec | |
|---|---|---|
| | Nitrogen Carrier | Mixed Carrier |
| 1 | 143 | 5218 |
| 2 | 253 | 5581 |
| 3 | 295 | 5480 |
| 4 | 358 | 6234 |
| 5 | 364 | 6279 |
| 6 | 386 | 5975 |
| 7 | 416 | 6587 |

EXAMPLE 3

Column Employed: Chromosil 310 (treated silica gel) Supelco Inc. in
  Six Foot Teflon® (FEP) ⅛" OD Tube
  Operated at 45° C. Nitrogen or Mixed carrier
  Gas Flowing at 40 cm³/min.
Sample employed 0.5 ppm Sulfur dioxide in Nitrogen balance gas. Sample volume ~2 cm³.

Sequential injections of this mixture onto the column according to a rigid time schedule, when using nitrogen and the mixed carrier gas (0.3 ppm Hydrogen sulfide/-Balance Nitrogen) give the following peak areas for sulfur dioxide.

|  | Peak Area, μV. sec | |
| --- | --- | --- |
| INJECTION | Nitrogen Carrier | Mixed Carrier |
| 1 | 212 | 1529 |
| 2 | 250 | 1636 |
| 3 | 249 | 1693 |
| 4 | 230 | 1661 |
| 5 | 235 | 1597 |

In each instance, the peak area for the sample can be converted to concentration of sulfur bearing compound in the sample by using the formula:

$$\frac{\text{(concentration of standard)}}{\text{(peak area of standard)}} \times \text{(peak area of sample)} = \text{concentration of sample}$$

wherein the peak area of a standard containing a particular sulfur bearing compound is developed by running the calibrated standard in the system under the same conditions at which the sample is run. In that manner, the concentration of components in a gaseous mixture can be accurately determined utilizing conventional chromatographic techniques.

The invention has been illustrated by the foregoing examples. However, they are not meant to be limiting as variations in materials and methods will be apparent to those skilled in the art without departing from the spirit and scope of this invention.

What is claimed is:

1. In a method for analyzing a gaseous sample containing sulfur bearing molecules in systems having sulfur reactive or adsorptive components, the improvement which comprises admixing said gaseous sample with a carrier gas consisting of a mixture of an analytically pure inert gas and an amount of a compound containing a nucleophilic sulfur atom effective to deactivate said components.

2. The improvement as in claim 1 wherein the compound is hydrogen sulfide, sulfur dioxide, a lower alkyl mercaptan, an aryl mercaptan, a lower alkyl sulfide, an aryl sulfide, an aryl disulfide, a lower alkyl disulfide or carbonyl sulfide.

3. The improvement as in claim 1 wherein the compound is hydrogen sulfide, sulfur dioxide, methyl mercaptan, carbon disulfide or carbonyl sulfide.

4. The improvement as in claim 1, 2 or 3 wherein said compound is present at a concentration of more than 0.05 parts per million and less than 2 parts per million on a volume basis in said carrier gas.

* * * * *